United States Patent [19]

Rinke

[11] Patent Number: 5,155,545
[45] Date of Patent: Oct. 13, 1992

[54] METHOD AND APPARATUS FOR THE SPECTROSCOPIC CONCENTRATION MEASUREMENT OF COMPONENTS IN A GAS MIXTURE

[75] Inventor: Günter Rinke, Weingarten, Fed. Rep. of Germany

[73] Assignees: Kernforschungszentrum Karlsruhe GmbH, Karlsruhe; Bernath Atomic GmbH & Co. KG, Wennigsen, both of Fed. Rep. of Germany

[21] Appl. No.: 620,705

[22] Filed: Dec. 3, 1990

[51] Int. Cl.$^5$ .................... G01J 3/00; G01N 21/31
[52] U.S. Cl. .................... 356/300; 356/326; 356/437; 250/345
[58] Field of Search ............. 356/300, 303, 320, 326, 356/432, 437, 438; 250/343, 339, 250, 345

[56] References Cited

U.S. PATENT DOCUMENTS

| 3,732,017 | 5/1973 | Wolber | 356/300 |
| 3,869,613 | 3/1975 | Link et al. | 250/343 |
| 4,849,637 | 7/1989 | Cerff et al. | 250/345 |

FOREIGN PATENT DOCUMENTS

| 2407133 | 8/1977 | Fed. Rep. of Germany . |
| 2326123 | 1/1979 | Fed. Rep. of Germany . |
| 2727976 | 5/1980 | Fed. Rep. of Germany . |
| 2924843 | 1/1981 | Fed. Rep. of Germany . |
| 2939733 | 4/1981 | Fed. Rep. of Germany . |
| 3624567 | 3/1988 | Fed. Rep. of Germany . |

OTHER PUBLICATIONS

Patent Abstracts of Japan, vol. 9, No. 127, [1850], May 31, 1985, 60-11,122, pp. 133, 360.
Luft, "Über einer neue Methode der registrierenden Gasanalyse mit Hilfe der Absorption ultraroter Strahlen ohne spektrale Zerlegung", Zeitschrift für technische Physik, No. 5, 1943, pp. 97-103.
Schaefer, "Ultrarot-Analysatoren und anderen Betriebsphotometer", VDI-Berichte No. 97, 1966, pp. 15-19.
Small et al, American Laboratory, vol. 20, Issue 11, 1988, pp. 89-91.

Primary Examiner—Vincent P. McGraw
Assistant Examiner—La Charles P. Keese, II
Attorney, Agent, or Firm—Spencer, Frank & Schneider

[57] ABSTRACT

A method for spectroscopically measuring a concentration of component gases in a gas mixture, wherein at least one component gas A has an absorption line spectrum and wherein the concentration of the gas A in the gas mixture exceeds the concentration of other component gases of the gas mixture to such an extent that measurement of the concentration of the other component gases would normally be interfered with by the gas A. The method includes the following steps: passing a beam of light of continuous spectrum through a measuring cuvette containing the gas mixture; introducing the beam of light from the measuring cuvette into a spectrometer which effects a spectral dispersion; introducing the dispersed light from the spectrometer into a detector; determining the concentration of component gases in the gas mixture from light intensities of absorption lines of the dispersed light sensed by the detector; charging an auxiliary gas cuvette with the gas A in such a concentration as to render the auxiliary gas cuvette light-impervious for wavelengths corresponding to absorption maxima of the gas A; and positioning the auxiliary gas cuvette containing the gas A in the beam of light upstream of the detector.

10 Claims, 7 Drawing Sheets

METHOD AND APPARATUS FOR THE SPECTROSCOPIC CONCENTRATION MEASUREMENT OF COMPONENTS IN A GAS MIXTURE

BACKGROUND OF THE INVENTION

This invention relates to a method and an apparatus for the spectroscopic measurement of concentrations of several components in a gas mixture. The gas mixture has at least one component A which has an absorption line spectrum and whose concentration in the gas mixture exceeds the concentrations of other components to such an extent that the measurement of the concentration of such other components is interfered with. Conventionally, a measuring cuvette is filled with the gas mixture and is irradiated by a continuous-spectrum light beam emitted by a light source. The light beam emanating from the measuring cuvette is guided through a spectrometer for spectral dispersion and is thereafter sensed by a detector. The concentration of the other components of the gas mixture is determined from the intensity of the absorption lines of the recorded light.

Thus, a light beam emanating from a light source is guided through a measuring cuvette which contains the gases to be examined. The light is absorbed by the components differently for different wavelengths, so that by measuring the light intensity before and after the passage of the light through the cuvette, the transmissions are determined for several wavelengths and the concentrations are determined by Lambert-Beer's law. The utilized wavelength range extends from the ultraviolet to the infrared wavelengths.

Such measuring instruments which are designated as spectral photometers, spectral spectrometers or array spectrometers are utilized in laboratory analyses and in the process measuring technology. These instruments permit a continuous measurement of gases, for example, for monitoring ammonia, sulfur dioxide and nitrogen oxides in the fumes of a fossil fuel power station or for an optimal control of systems for the removal of nitrogen.

Apparatus which include instruments of the above-outlined type have been marketed by numerous firms for laboratory use. Also, apparatus usable in manufacturing processes are obtainable. Some of these utilize ultraviolet lamps with a continuous emission spectrum, such as deuterium and xenon lamps.

Thus, German Offenlegungsschrift (application published without examination) 36 24 567 describes an analyzing system for the measuring of NO and $SO_2$ which includes a deuterium lamp as the ultraviolet light source, a spectrometer and a photodiode array as a detector.

The periodical American Laboratory, (Volume 20, Issue 11, 1988, pages 88-91) describes a similar system which utilizes the same measuring principle.

These types of process measuring apparatus are utilized, for example, in power plants for monitoring the emission of ammonia, sulfur dioxide and nitrogen oxides. These known systems, however, function satisfactorily only in a limited range of concentration. Thus, for example, it is known that at high $SO_2$ concentrations of approximately 1500 ppm, a strong background absorption in the ultraviolet range results, adversely affecting the measuring accuracy.

German Patent No. 27 27 976 discloses an apparatus for measuring at least one component of a gas mixture. The auxiliary cuvette of the apparatus contains a component B to be measured, rather than an interfering component A. The auxiliary cuvette is situated either continuously in the reference beam or is periodically pivoted thereinto.

The concentration of the component B is calculated from the difference between the measuring beam and the reference beam intensities or from the consecutive intensity values of the recorded measuring and reference beams.

SUMMARY OF THE INVENTION

It is an object of the invention to provide an improved method and apparatus of the above-outlined type in which the influence of an interfering component present in a high concentration is eliminated if such an interfering component has a narrow absorption line spectrum.

It is a further object of the invention to provide an improved apparatus with which errors caused by the limited resolution capability of the spectrometer may be eliminated so that the concentrations of gases in a gas mixture may be reliably determined even if the gas mixture has at least one component in excessive concentration.

This object and others to become apparent as the specification progresses, are accomplished by the invention, according to which, briefly stated, an auxiliary gas cuvette is placed in the path of the light beam between the light source and the detector; the auxiliary gas cuvette contains the component or components A in such a concentration that the auxiliary gas cuvette becomes light-impervious for those wavelengths which correspond to the absorption maxima of the component or components A.

Thus, the low accuracy of the conventional apparatus in the presence of a high-concentration, interfering component A may be improved upon if the component A has a sharp line structure and the resolution capability of the spectrometer is not sufficient to resolve the lines. A poor resolution capability which may not be improved because of the light intensity, because the often large spectral range which has to be detected in its totality and because of the involved costs, leads to the fact that all lines of the gas appear significantly broader than they are in reality. This results in overlaps and an only apparently continuous background. Concentrations which are computed on the basis of such an untrue spectrum are therefore erroneous.

The above-described effect may thus be reduced if the line width of the interfering component A is smaller than the transmission width of the spectrometer. For obtaining such a reduction, according to the invention, an auxiliary cuvette which contains the interfering gas A, for example, $SO_2$, is placed in the path of the measuring beam. In case the concentration of such a gas and the cuvette length are properly selected, the auxiliary gas cuvette is light-impervious for those wavelengths on which the maxima of the absorption lines of component A lie. Changes in the concentration of the component A in the measuring cuvette can thus no longer have a transverse sensitivity, because the spectrometer and detector ignore that radiation which is characteristic for the component A.

In case the component A is not only an interfering component whose concentration is of no interest, but should also be measured, then such measurement may be achieved at another wavelength where the absorption coefficient of the component A should be so small that the auxiliary gas cuvette is light-pervious. The absorption spectrum may also be continuous in that location. While the limit of detection is, to be sure, worse for such a component than without an auxiliary gas cuvette, such a fact, however, should in general not have a disturbing effect at high concentrations of the component A. If permitted by the measuring process and the particular use, the auxiliary gas cuvette is brought into the measuring beam only periodically or for predetermined times.

The above-outlined measuring process is to be distinguished from non-dispersive (NDIR) process photometers with gas filter correlation, such as described in German Patent 27 27 976 as used in the NDIR process photometers in the infrared range. In these apparatus it is the component B to be measured (rather than the interfering component A) which is, in an auxiliary gas cuvette, placed either continuously in the path of a reference beam or periodically in the path of a measuring beam.

The advantages of the invention reside in the lowered transversal sensitivity, the reduced background which makes possible for other gases (gases in traces) a longer measuring path and a mechanically rigid measurement arrangement which is well adapted for the process measuring technology.

DESCRIPTION OF THE PREFERRED EMBODIMENTS

Figure 1:
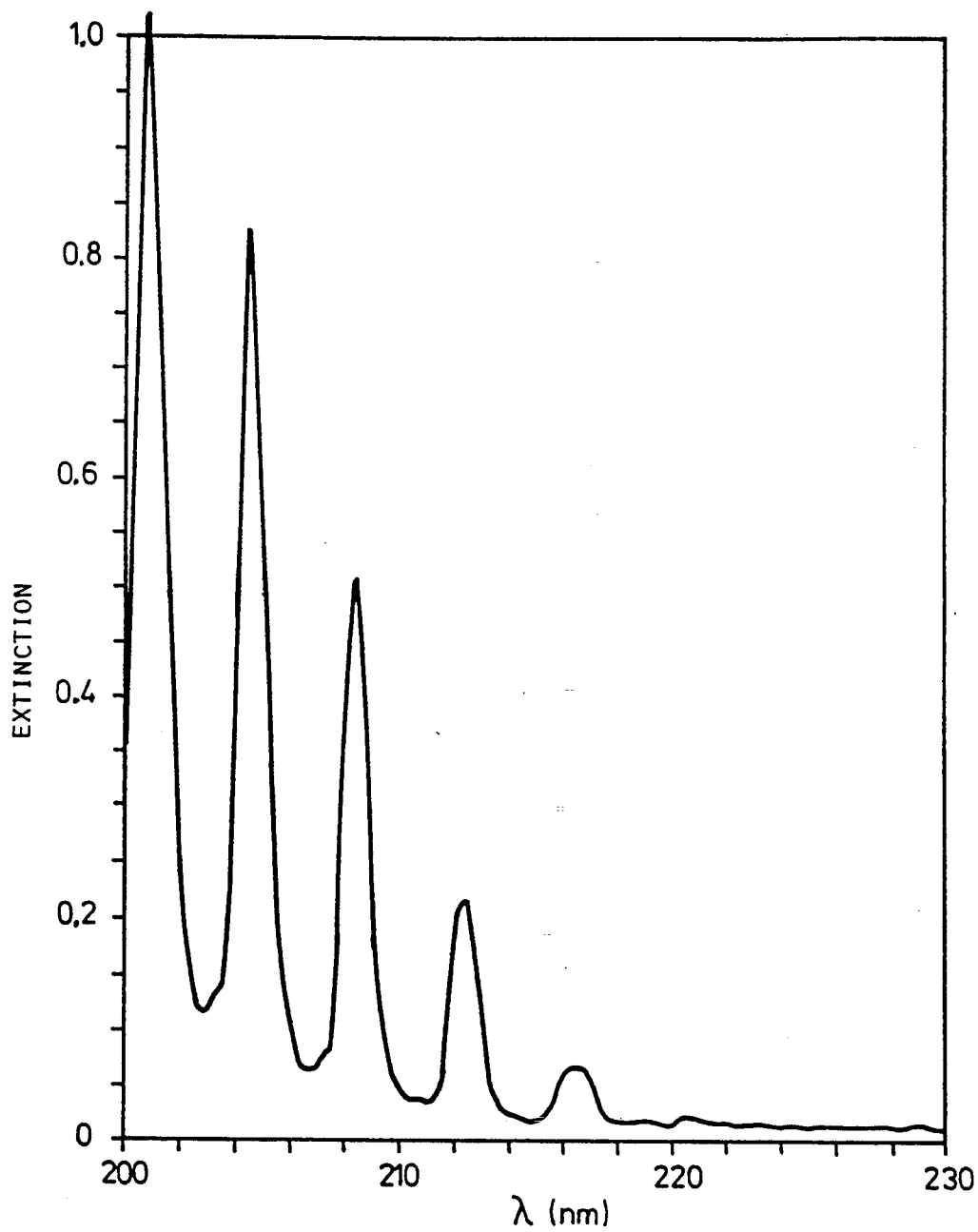
FIG. 1 is a diagram illustrating an ultraviolet absorption spectrum of 815 ppm $NH_3$.

FIG. 1 illustrates a measured absorption spectrum of 815 ppm $NH_3$ obtained with a laboratory photospectrometer and a 10 cm cuvette in throughflow. The line structure can be well recognized.

Figure 2:
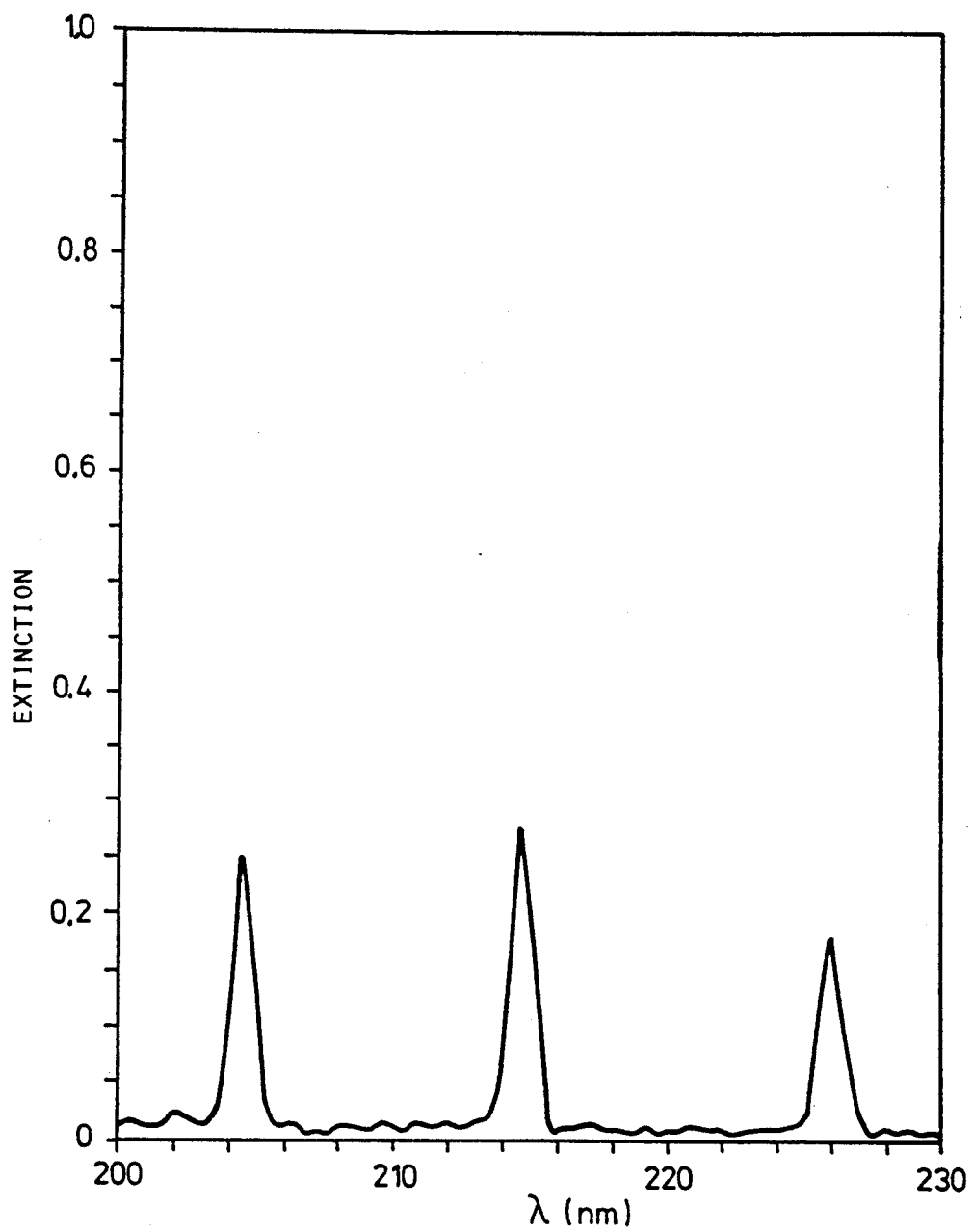
FIG. 2 is a diagram illustrating an ultraviolet absorption spectrum of 1425 ppm NO.

FIG. 2 illustrates an ultraviolet absorption spectrum of 1425 ppm NO which was obtained under the same conditions as described in connection with FIG. 1. In FIG. 2 also, the typical line structure may be well recognized.

Figure 3:
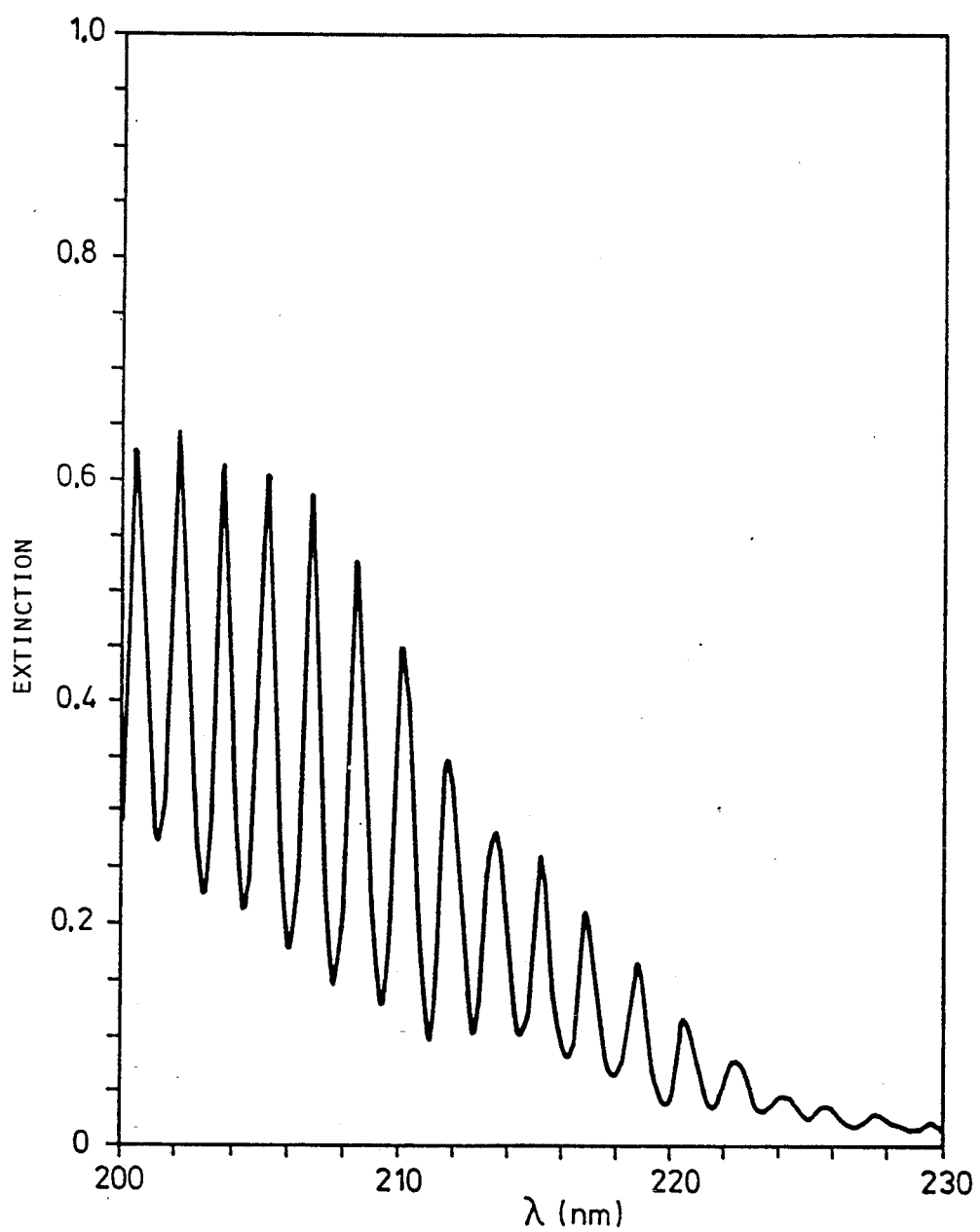
FIG. 3 is a diagram illustrating an ultraviolet absorption spectrum of 615 ppm $SO_2$.

In FIG. 3 the absorption of 615 ppm $SO_2$ is similarly illustrated where the line structure may also be recognized. The distances between the lines, however, are significantly less and show an apparent continuity.

Figure 4:
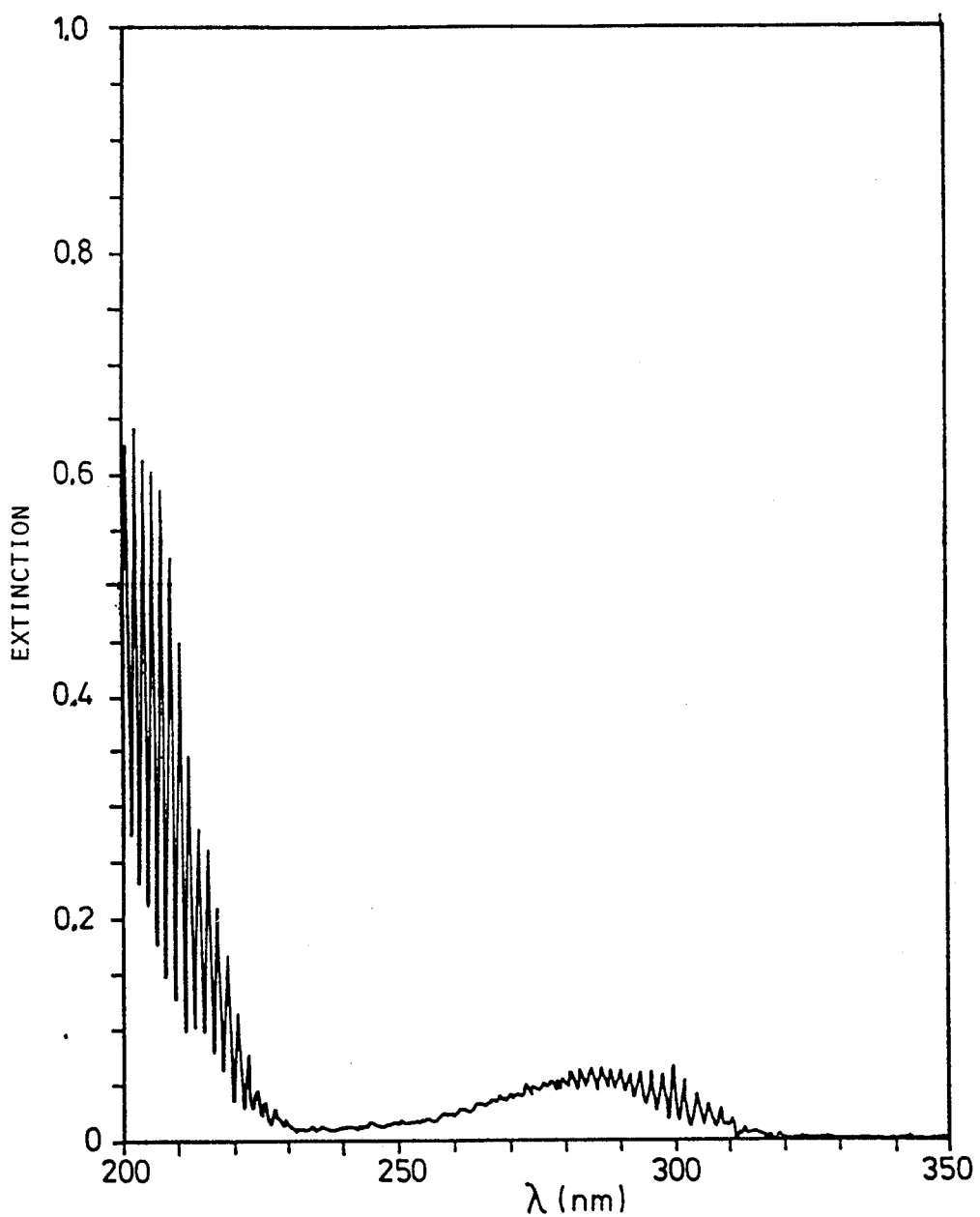
FIG. 4 is a diagram similar to FIG. 3 showing the abscissa on a different scale.

For supporting the description which follows, in FIG. 4 there is shown, with a change in scale, the same spectrum as in FIG. 3. It is noted in particular that at 280 nm there is obtained a zone with true continuous absorption which, to be sure, is smaller than the absorption bands of shorter wavelength.

The width of the lines is determined solely by the selected spectral bandwidth of 0.5 nm of the laboratory spectral photometer used. In case an even smaller spectral bandwidth is set, merely narrower lines can be obtained. The practical limit in this apparatus is at 0.1 nm, at which even a fine structure may be recognized. Static noise, however, also increases. The real, physical limit is determined solely by the Doppler and pressure broadening which, however, is significantly smaller than the typical spectral bandwidth (1 nm) of process spectrometers. The apparent continuity too, is rooted in the limited resolution capability of the spectral photometer used and is merely a superposition of the line wings.

Figure 5:
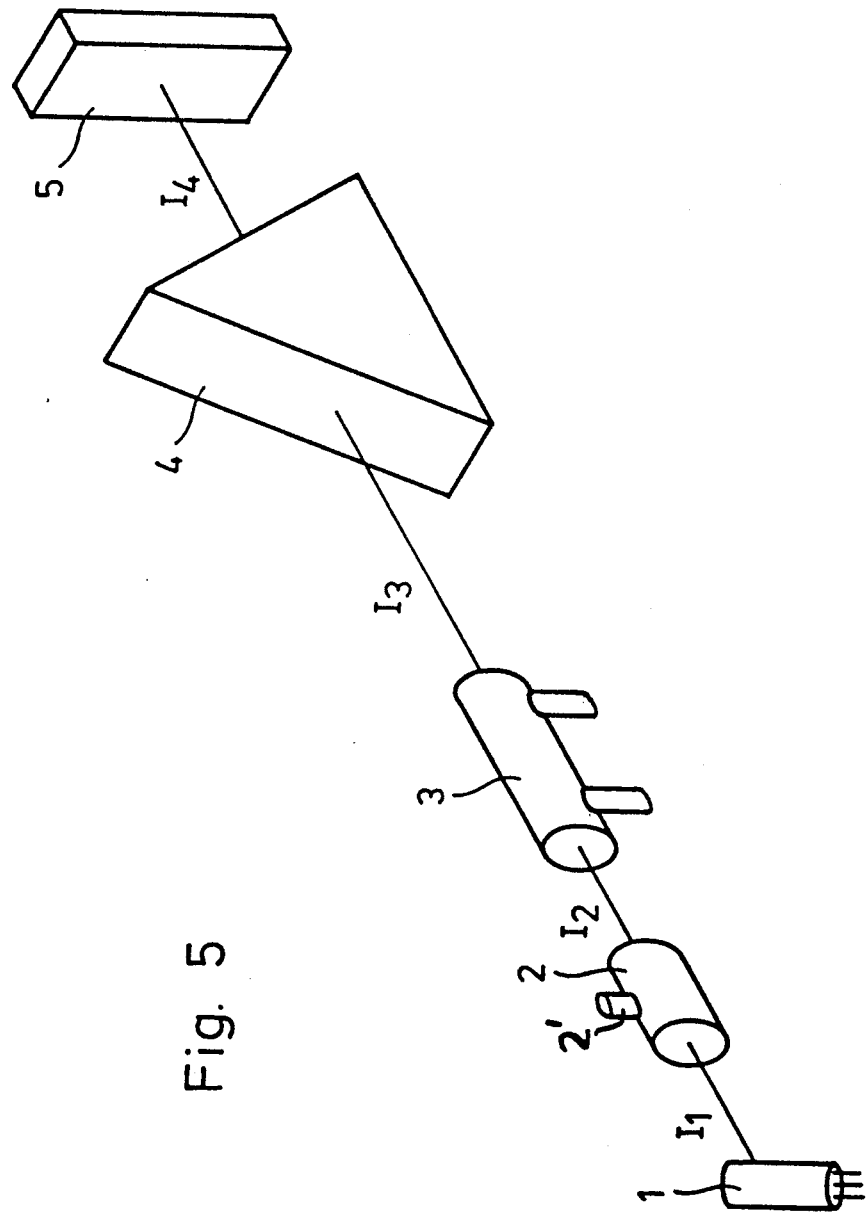
FIG. 5 is a schematic perspective view of an apparatus according to the invention.

FIG. 5 illustrates a measuring apparatus according to the invention. The apparatus includes an ultraviolet lamp 1, a closed auxiliary gas cuvette 2, a throughflow measuring cuvette 3, a spectrometer 4 and an optical detector 5. The latter is preferably of a linear array or a two-dimensional array type.

The auxiliary gas cuvette 2 is charged with the gas, for example, $SO_2$, whose interfering effect is to be reduced. The measuring cuvette 3 contains, for example, $SO_2$, NO and $NH_3$.

Thus, in order to render the auxiliary gas cuvette 2 light-impervious at the line maxima, concentration and length have to be correctly selected. For this purpose first the wavelength range is determined which is to be used for the concentration measurement. In case of measuring NO, $NH_3$ and $SO_2$ in fumes, a range of 200 nm to 230 nm is appropriate because all three components have strong absorption lines in that range. Because of the steeply increasing $SO_2$ absorption below 215 nm and the important, analytically useful lines of $NH_3$ and NO which lie precisely in that range, the optimal charge of the auxiliary gas cuvette 2 is calculated for such a wavelength of 215 mm.

From the spectrum of 615 ppm $SO_2$ (illustrated in FIG. 3) contained in a 10-cm auxiliary cuvette 2', the concentration for which the transmission is 1% at 215 nm may be computed based on Lambert-Beer's law. In practice, transmission values below 5%, preferably about 1% may be used. The optimal value for the transmission is dependent from the noise behavior of the spectrometer and the detector. This value should be maintained at such a magnitude that it corresponds in percentage to the noise of the spectrometer system. Conventional spectrometers are capable of measuring accurately only a transmission down to 1%, due to their noise generation. Lambert-Beer's law is $$T = 10^{-E} = 10^{-\epsilon c d}$$

wherein
 E is the decimal extinction,
 $\epsilon$ is the decimal extinction coefficient,
 c is the concentration and
 d is the layer thickness.

From the decimal extinction E=0.3 at a layer thickness d=10 cm and a concentration c=615 ppm there may be calculated the concentration copt for an extinction $E_{opt}=2$ which corresponds to a transmission of 1%, at an identical layer thickness:

$$C_{opt} = 2 \, c/E = 2 \cdot 615 \, ppm/0.3 = 4100 \, ppm = 0.41\%$$

If, for practical reasons a 1-cm cuvette is preferred, then the concentration has to be ten-fold.

In a practical embodiment, for the auxiliary gas cuvette 2 there may be utilized a quartz cuvette having a diameter of 2 cm and an optical length of 1 1 cm. Such a cuvette may be made from a quartz tube having an outer diameter of 2 cm and a wall thickness of 2 mm; the component is fused at each end with a quartz window having a diameter of 2 cm and a wall thickness of 2 mm. This auxiliary gas cuvette is charged through a nipple 2' which is fused to the quartz tube. First, the cuvette is evacuated and heated. Thereafter the cuvette 2 is charged first with $SO_2$ and then with $N_2$ such that a concentration of 4.1% $SO_2$ is obtained in $N_2$. Then the cuvette is sealed by fusing shut the charging nipple 2'.

Figure 6:
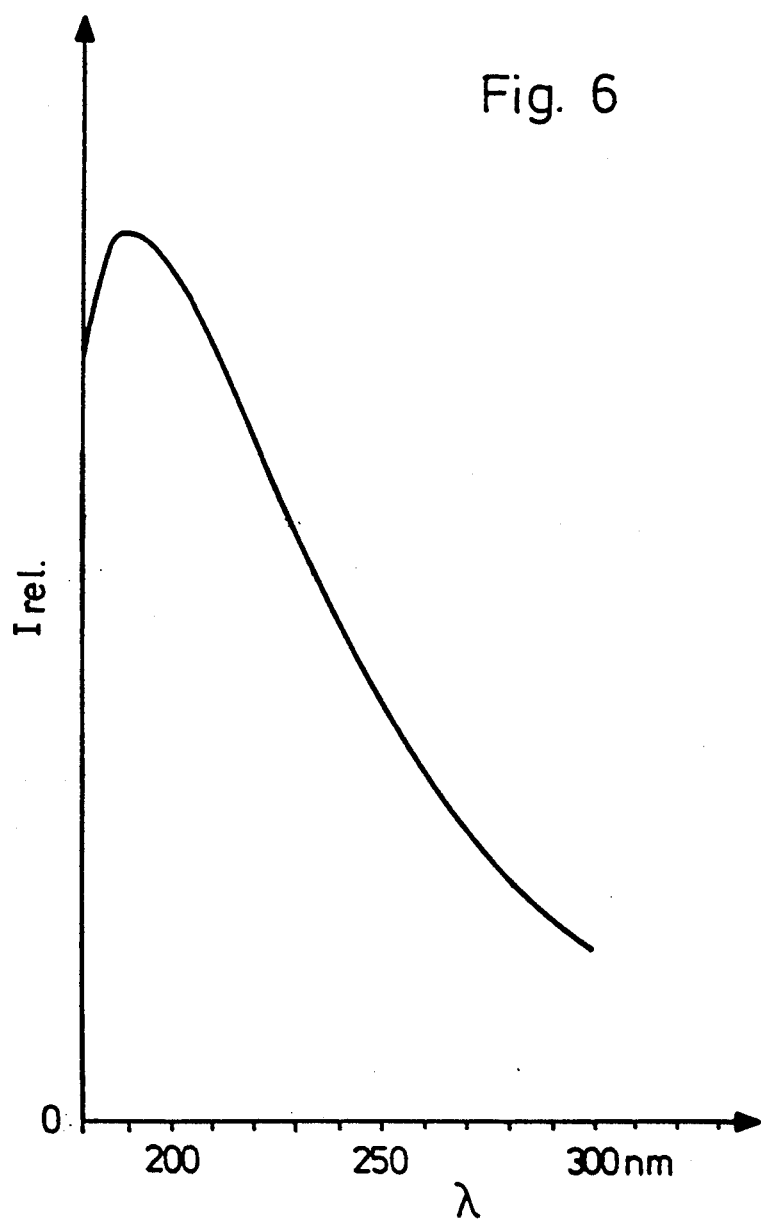
FIG. 6 is a diagram illustrating an emission spectrum of a deuterium lamp used in the apparatus according to the invention.
Figure 7A:
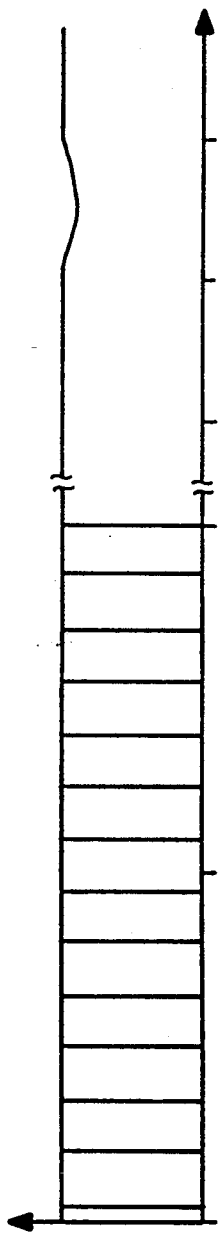
FIGS. 7a & 7b are diagrams illustrating light intensities occurring inside the measuring apparatus according to the invention.
Figure 7B:
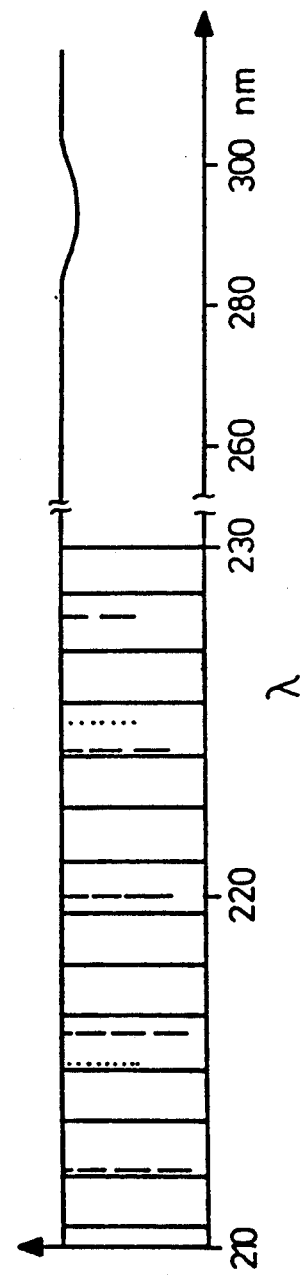

For further supporting the explanation of the principle utilized, in FIGS. 6, 7a and 7b there are schematically illustrated the light intensities at various wavelengths. FIG. 6 shows a typical emission spectrum of a deuterium lamp which is often utilized in the ultraviolet spectral range. A continuous emission may be observed which above 200 nm becomes weaker as the wavelength increases. Instead of a deuterium lamp, other ultraviolet lamps with continuous spectrum (such as a xenon lamp) may be utilized.

The emission spectrum is changed by the following optical components as shown in FIG. 5:

The light which is generated by the ultraviolet lamp 1 and which has an intensity $I_1$ and a continuous spectrum, is in a characteristic fashion partially weakened in the auxiliary ga cuvette 2 and in the measuring cuvette 3 so that downstream of these components a light having respective intensities $I_2$ and $I_3$ is obtained. $I_4$ designates the light intensities which are changed by the limited resolution capability of the array spectrometer.

FIGS. 7a, 7b show the light intensities normalized to the spectrum of the ultraviolet lamp 1 as a function of the wavelength in nm. The abscissa is interrupted at approximately 230 nm and the scale is changed so that spectrum at 290 nm may be still illustrated. The transmission is determined by dividing by a reference spectrum.

FIG. 7a shows the transmission which is modified by the auxiliary gas cuvette 2 and which is obtained by division of the spectrum of $I_2$ by $I_1$. The transmission shows at the wavelengths up to 230 nm which characterizes $SO_2$, such strong discrete absorption lines that in that range no light is transmitted. At about 290 nm the $SO_2$ absorption is less so that light is still transmitted there.

FIG. 7b shows the transmission of the light $I_3/I_1$ which leaves the measuring cuvette 3 and which is modified by the cuvettes 2 and 3—with the characteristic absorption lines of $SO_2$, NO and $NH_3$. The absorption lines for $SO_2$ are shown as solid lines, those for $NH_3$ are dashed lines and those for NO are dotted lines. This transmission is obtained by multiplying the transmission of the auxiliary gas cuvette 2 (FIG. 7a) with the transmission of the measuring cuvette 3. The transmission of the measuring cuvette 3 is obtained from the concentrations of the gases NO, $NH_3$ and $SO_2$ contained in the measuring cuvette 3. If, for example, the three gases with the concentrations as shown in FIGS. 1, 2 and 3 are introduced into the measuring cuvette 3, the spectra of FIGS. 1-3 must be added to one another and recalculated based on Lambert-Beer's law to obtain transmission.

It is to be noted that the NO and $NH_3$ lines are transmitted by the auxiliary gas cuvette 2 substantially unchanged, while the intensity at the locations of the $SO_2$ lines is practically zero. A change of the $SO_2$ concentration in the measuring cuvette 3 cannot be detected, nor does it interfere with the other lines.

In case the auxiliary gas cuvette 2 is omitted, all $SO_2$ lines would be transparent, corresponding to the $SO_2$ concentration. In such a case, particularly a differentiation between $SO_2$ lines and $NH_3$ lines at typical spectral bandwidth of process spectrometers of 1 nm would not be practically feasible and thus the computation of concentration would be erroneous.

In the embodiment described the wavelength range between 280 and 300 nm may be used for determining the concentration of $SO_2$ because in that range the auxiliary gas cuvette 2 is sufficiently light-pervious.

The described embodiment may be altered in several aspects. The auxiliary gas cuvette need not be necessarily disposed at the location as shown in FIG. 5. It may be situated anywhere between the ultraviolet lamp I and the detector 5, that is, it may be placed inside the spectrometer 4. Stated differently, the auxiliary gas cuvette may be situated in the light beam anywhere upstream of the detector, as viewed in the direction of the propagation of the light beam.

The single beam arrangement assumed in the described embodiment is not necessarily required for practicing the principle; a two-beam arrangement may be used as well.

Further, the auxiliary gas cuvette need not necessarily be rigidly maintained in the optical beam path; it may be shifted or pivoted into the beam path for predetermined periods or in a cyclical manner. Such a temporary presence of the auxiliary gas cuvette is particularly advantageous if the interfering component should also be measured and no weaker absorption is present than in case of $SO_2$. In such case the interfering component may be measured during periods when the auxiliary gas cuvette is externally of the light beam, whereas the other components are measured when the auxiliary gas cuvette is placed in the light beam.

It will be understood that the above description of the present invention is susceptible to various modifications, changes and adaptations, and the same are intended to be comprehended within the meaning and range of equivalents of the appended claims.

What is claimed is:

1. In a method for spectroscopically measuring a concentration of component gases in a gas mixture, wherein at least one component gas A has an absorption line spectrum and wherein the concentration of the gas A in the gas mixture exceeds the concentration of other component gases of the gas mixture to such an extent that measurement of the concentration of said other component gases would normally be interfered with by the gas A, including the steps of passing a beam of light, generated by a light source as a light of continuous spectrum, through a measuring cuvette containing said gas mixture;

introducing said beam of light from the measuring cuvette into a spectrometer;

effecting spectral dispersion of the beam of light in the spectrometer;

introducing the dispersed light from the spectrometer into a detector; and determining the concentration of component gases in the gas mixture form light intensities of absorption lines of the dispersed light sensed by the detector;

the improvement comprising the steps of (a) charging an auxiliary gas cuvette with the gas A in such a concentration as to render the auxiliary gas cuvette light-impervious for wavelengths corresponding to absorption maxima of said gas A, whereby the light beam exiting form the auxiliary cuvette is void of spectral lines corresponding to absorption lines of said gas A; and (b) positioning said auxiliary gas cuvette containing said gas A in the beam of light upstream of said detector as viewed in a direction of propagation of the beam of light.

2. A method as defined in claim 1, wherein said gas A is formed of at least one of the gases selected from a group consisting of $SO_2$, $NH_3$, NO, CO and $CO_2$.

3. A method as defined in claim 1, further comprising the step of determining the concentration of the gas A in the gas mixture from light intensities at light wavelengths for which said auxiliary gas cuvette is light-pervious.

4. An apparatus for spectroscopically measuring a concentration of component gases in a gas mixture, wherein at least one component gas A has an absorption line spectrum and wherein the concentration of the gas A int eh gas mixture exceeds the concentration of other component gases of the gas mixture to such an extent that measurement of the concentration of said other component gases would normally be interfered with by the gas A, comprising (a) a light source generating a beam of light having a continuous spectrum and a predetermined path;

(b) a measuring cuvette, containing the gas mixture, situated in said path;

(c) a spectrometer situated in said path and being arranged for receiving and dispersing the beam of light after passage thereof through said measuring cuvette;

(d) a detector situated in said path and being arranged for receiving the beam of light after passage thereof through said spectrometer and being arranged for determining the concentration of component gases of the gas mixture from light intensities of absorption lines of the light dispersed by the spectrometer; and (e) a sole auxiliary gas cuvette; said sole auxiliary gas cuvette being placed in said path between the light source and the detector; said sole auxiliary gas cuvette containing the gas A in such a concentration as to render the sole auxiliary gas cuvette light-impervious for wavelengths corresponding to absorption maxima of the gas A, whereby the light beam exiting from the sole auxiliary cuvette is void of spectral lines corresponding to absorption lines of said gas A.

5. An apparatus as defined in claim 4, wherein said gas A is sealed in said auxiliary gas cuvette.

6. An apparatus as defined in claim 5, wherein the A is formed of at least one of the gases selected from the group consisting of $SO_2$, $NH_3$, NO, CO and $CO_2$.

7. A method as defined in claim 1, wherein said spectrometer is an array spectrometer.

8. An apparatus as defined in claim 4, wherein said spectrometer is an array spectrometer.

9. A method as defined in claim 1, wherein said light source is a sole light source, said measuring cuvette is a sole measuring cuvette and said auxiliary gas cuvette is a sole auxiliary gas cuvette.

10. An apparatus as defined in claim 4, wherein said light source is a sole light source, said measuring cuvette is a sole measuring cuvette and said auxiliary gas cuvette is a sole auxiliary gas cuvette.

* * * * *